United States Patent [19]

Flick

[11] Patent Number: 6,087,549
[45] Date of Patent: Jul. 11, 2000

[54] MULTILAYER LAMINATE WOUND DRESSING

[75] Inventor: A. Bart Flick, Lakemont, Ga.

[73] Assignee: Argentum International, Roswell, Ga.

[21] Appl. No.: 08/935,026

[22] Filed: Sep. 22, 1997

[51] Int. Cl.[7] .................................................. A61F 13/00
[52] U.S. Cl. .......................... 602/41; 428/103; 428/294.1
[58] Field of Search ............................... 602/41; 428/412, 428/103, 294.1

[56] References Cited

U.S. PATENT DOCUMENTS

| | | | |
|---|---|---|---|
| 3,964,477 | 6/1976 | Ellis et al. | 128/172.1 |
| 4,027,393 | 6/1977 | Ellis et al. | 32/10 |
| 4,291,125 | 9/1981 | Greatbatch | 435/240 |
| 4,313,438 | 2/1982 | Greatbatch | 128/207.21 |
| 4,476,590 | 10/1984 | Scales et al. | 3/1.91 |
| 4,563,184 | 1/1986 | Korol | 604/368 |
| 4,728,323 | 3/1988 | Matson | 604/304 |
| 4,747,845 | 5/1988 | Korol | 604/368 |
| 4,757,804 | 7/1988 | Griffith et al. . | |
| 4,767,401 | 8/1988 | Seiderman . | |
| 4,781,705 | 11/1988 | Shepherd et al. . | |
| 4,817,594 | 4/1989 | Juhasz | 128/155 |
| 4,886,505 | 12/1989 | Haynes et al. | 604/265 |
| 4,889,530 | 12/1989 | Smith et al. | 604/304 |
| 4,911,688 | 3/1990 | Jones . | |

(List continued on next page.)

OTHER PUBLICATIONS

"Electric Fields and Wound Healing" by Lionel F. Jaffe, Ph.D. and Joseph W. Vanable, Jr., Ph.D., Clinics in Dermatology, Jul.–Sep. 1984, vol. 2, No. 3, pp. 34–44.

"Measurement of Electrical Currents Emerging During the Regeneration of Amputated Finger Tips in Children" by Cynthia M. Illingworth and A.T. Barker, Clin. Phys. Physiol. Meas., 1980, vol. 1, No. 1, pp. 87–89.

"Human Skin Battery Potentials and Their Possible Role in Wound Healing", by I.S. Foulds and A.T. Barker, British Journal of Dermatology (1983) 109 pp. 515–522.

"Antibacterial Effects of Silver Electrodes with Weak Direct Current", by J.A. Spadaro, T.J. Berger, S.D. Barranco, S.E. Chapin and R.O. Becker, Antimicrobial Agents and Chemotherapy, Nov. 1974, pp. 637–642.

"Antifungal Properties of Electrically Generated Metallic Ions", by T.J. Berger, J.S. Spadaro, Richard Bierman, S.E. Chapin and R.O. Becker, Antimicrobial Agents and Chemotherapy, Nov. 1976, pp. 856–860.

"Bioelectric Potentials in Bone", by Z.B. Friedenberg, M.D. and Lieutenant Commander Carl T. Brighton, Medical Corps., United States Navy, The Journal of Bone and Joint Surgery, vol. 48–A, No. 5, Jul. 1966.

"Integumentary Potentials and Wound Healing" by Joseph W. Vanable, Jr., Electric Fields in Vertabrate Repair, 1989, pp. 171–224.

"Studies with Different Types of Visual Analog Scales for Measurement of Pain" PAIN—The Journal of the International Association for the Study of Pain, vol. 1, No. 4, Dec. 1975.

Westaim Biomedical Commercial Literature, bearing 1998 Copyright notice and product label bearing Acticoat®.

*Primary Examiner*—Michael A. Brown
*Assistant Examiner*—Kelvin Hart
*Attorney, Agent, or Firm*—Selitto & Associates

[57] ABSTRACT

A multilayer laminate wound dressing comprising a plurality of layers of preferably silver or silver-coated fibers in a woven fabric alternating with layers of nonconductive, preferably nonmetallic, fabric. Each layer preferably contains a different ratio of metalized to nonmetalized fibers. The metalized fibers are preferably made of or coated with silver. The dressing promotes healing by stimulating cellular de-differetiation, followed by cellular proliferation. The dressing also has antibacterial, antifungal and analgesic properties.

24 Claims, 13 Drawing Sheets

U.S. PATENT DOCUMENTS

| | | | |
|---|---|---|---|
| 4,984,570 | 1/1991 | Langen et al. | 128/156 |
| 4,990,144 | 2/1991 | Blott | 604/304 |
| 4,997,425 | 3/1991 | Shioya et al. | 604/304 |
| 5,049,139 | 9/1991 | Gilchrist . | |
| 5,147,338 | 9/1992 | Lang et al. | 604/304 |
| 5,158,555 | 10/1992 | Porzilli . | |
| 5,292,589 | 3/1994 | Shepherd et al. . | |
| 5,340,363 | 8/1994 | Fabo . | |
| 5,374,283 | 12/1994 | Flick . | |
| 5,429,590 | 7/1995 | Saito et al. | 602/48 |
| 5,454,886 | 10/1995 | Burrell et al. . | |
| 5,470,585 | 11/1995 | Gilchrist . | |
| 5,512,041 | 4/1996 | Bogart . | |
| 5,571,079 | 11/1996 | Bello et al. | 602/46 |
| 5,571,521 | 11/1996 | Lasker | 424/409 |
| 5,607,683 | 3/1997 | Capelli | 424/405 |
| 5,681,575 | 10/1997 | Burrell et al. . | |
| 5,695,857 | 12/1997 | Burrell et al. . | |
| 5,753,251 | 5/1998 | Burrell et al. . | |
| 5,770,255 | 6/1998 | Burrell et al. . | |
| 5,782,788 | 7/1998 | Widemire . | |
| 5,814,094 | 9/1998 | Becker et al. . | |

MULTILAYER LAMINATE WOUND DRESSING

FIELD OF THE INVENTION

The present invention relates to wound dressings, and more particularly to a multilayer laminate structure formed of layers of a mesh material, each layer containing a different ratio of metalized to nonmetalized fibers. The metalized fibers are preferably made of silver. The dressing promotes healing and also has antibacterial and antifungal efficacy.

BACKGROUND OF THE INVENTION

Wound treatment has become a more highly developed area of scientific and commercial investigation as new research has revealed the workings of the healing process. More rapid healing of a wound reduces long term healthcare costs and improves patient recovery, including regaining of sensation, function and aesthetics.

Healing, like all other biological processes, is a cellular process. The occurrence of an injury immediately triggers the onset of this process, which continues until the injury is healed. Although its exact mode of action is not yet understood, it is clear that a feedback mechanism monitors the extent of tissue damage and adjusts cellular activity in the injured area to produce the exact amount of healing needed.

As used herein, the terms "wound" and "injury" refer to tissue damage or loss of any kind, including but not limited to, cuts, incisions (including surgical incisions), abrasions, lacerations, fractures, contusions, burns, amputations and the like.

Healing processes can be classified into three types, determined by how the cells in the injured area react to the injury. The simplest type of healing is scarification healing, wherein cells at the edges of a wound produce collagen and elastic fibers which simply bind the edges of the wound together without restoring severed nerves or blood vessels. This type of healing produces a visible scar, and sometimes results in numbness and circulatory inadequacy in the region of the wound and regions distal thereto. In the higher animals, including man, the heart, skeletal muscle, and nerve tissue (including the brain) heal by scarification.

A second type of healing is tissue replacement, wherein the cells of some body tissues produce more cells of their own kind to replace missing portions. In humans, the skin and portions of the gastrointestinal tract heal by replacement. In this type of healing, the replacement rate of the cells in the injured area increases to produce sufficient numbers of cells to help heal the injury, then returns to normal after healing is complete. Replacement is effective only if enough normal cells of the needed types are present in the area, and only for the particular types of cells that are capable of healing in this manner. Replacement is often inadequate for healing full-thickness skin wounds, which frequently heal with limited re-epithelialization, resulting in poorly innervated, thin and inelastic skin, while subcutaneous soft tissue defects heal primarily by scarification. However, such results are generally adequate for function if the wound is on the torso or the extremities (excepting the hand).

The most effective—and most complex—type of healing is regeneration. This type of healing is capable of replacing entire limbs and internal organs, and even portions of the brain and heart, which typically contain multiple types of cellular structures. Regeneration is a biphasic process. In the first phase, normal, mature "differentiated" cells at the site of the injury revert to an embryonic, unspecialized form ("de-differentiated cells"). These de-differentiated cells multiply rapidly, then become activated and demonstrate a variety of energetic processes which may include amitotic division, nuclear transfer, migration of free nuclei into residual tissues, and production of exceptionally large cells containing nuclear material from a number of individual de-differentiated cells (thus, "activated cells" are cells that undergo these processes). It is also believed that de-differentiated cells have a longer lifespan than differentiated cells.

Activation results in the rapid accumulation of a large mass of embryonic cells known as the blastema, which is the essential element for regeneration. The blastema may be viewed as providing the biological raw material needed for rebuilding the missing tissues. Formation of an adequately sized blastema results in complete regeneration of the missing tissues, whereas if the blastema is inadequate in size, only partial or incomplete regeneration takes place (formation of a stunted or incomplete part, or merely regeneration of individual tissue types that are not fully organized into the desired structure).

In the second phase of the regeneration process, the embryonic cells of the blastema respecialize ("re-differentiate") into the various types of cells needed to rebuild the missing tissues and organized structures in complete anatomical detail. The rebuilding process is essentially a recapitulation (albeit on a local scale) of the original embryonic development of the tissues being replaced.

In vertebrates, regenerative healing is found in certain species of amphibians (notably salamanders). It is almost totally lacking in humans, except in the fetus and in very young children (who may regenerate the distal finger tip if the wound is left open). In adults, regeneration is largely limited to parts of the fracture healing process. Clearly, it would be beneficial if humans could regenerate other damaged tissues, both in terms of more cost-effective treatment modalities and improved outcomes for patients.

The stimulus which initiates the complex regenerative process in amphibians has been reported to be a specific type of electrical signal, but the mechanism which provides the blueprint for the tissues to be regenerated is largely unknown. In the case of regeneration of individual tissues, however, a number of inducer substances that carry a specific signal causing either embryonic, de-differentiated, or mature cells to convert into specific tissue types have been identified. These "biological inducers" are analogous to chemical catalysts in that they effect cellular transformation by contact with the cells, but the inducer itself does not take part in the transformation. According to one theory, it is believed that biological inducers act by producing a signal in the nature of a specific electrical field which causes an event to occur on the surface of the target cell, which in turn causes the DNA in the target cell to alter the cell type in a specific fashion. By way of example, a "bone induction material" that causes the transformation of muscle cells into bone has been identified (M. Urist, Proc. Nat. Acad. Sci. USA, Vol. 70, pp. 3511–3515 (1973)).

Healing in general is known to be related to the degree of the injury, the amount of nerve tissue present at the site, and the electrical potential difference between the site and surrounding intact tissue (the "current of injury"). In particular, regeneration in amphibians such as salamanders and fracture healing in mammals are associated with complex changes in the local DC (direct current) electric field. An injury results in changes in the electric field and stimulates the animal's neural system, which in turn produces an electrical signal at the site of the injury, stimulating the complex cellular responses that eventually produce healing. The electric field gradually returns to normal, pre-injury levels as the injury heals. Conversely, failure of the normal healing process, as in fracture nonunions, is associated with the absence of appropriate electrical signals at the site of the injury.

The antimicrobial and antifungal properties of silver and silver compounds are well known. Topical preparations that contain silver or silver compounds-silver nitrate solution, silver sulfadiazine cream, colloidal silver compositions, silver-protein compounds such as Argyrol™, and so forth, are widely used in medicine. The useful effects of these compositions are due to the small amounts of free silver ions produced by dissociation of the silver compound or to formation of toxic byproducts in situ.

The effectiveness of silver as an antimicrobial agent is at least partly determined by the delivery system. Most silver compounds that dissociate readily and produce large numbers of free silver ions are highly toxic to mammalian (including human) tissues Less-toxic compounds, including silver sulfadiazine cream (widely used in the treatment of burns) and silver nitrate solution, do not dissociate readily and therefore do not release large numbers of silver ions. These compounds must be re-applied frequently to maintain their clinical efficacy.

Electrically-generated silver ions, which can penetrate more deeply into the tissues, are effective even against antibiotic-resistant strains of bacteria, fungi, etc., inhibiting growth in vivo and in vitro at current densities as low as 10 $nA/mm^2$ and silver ion concentrations as low as 0.5 mg/ml. The effects of electrically-generated silver ions are described in a number of publications, including the following: J. A. Spadaro et al., "Antibacterial Effects of Silver Electrodes with Weak Direct Current," Antimicrobial Agents & Chemotherapy, Vol. 6, pp. 637–642 (1974); T. J. Berger et al., "Antifungal Properties of Electrically Generated Metallic Ions," Antimicrobial Agents & Chemotherapy, Vol. 10, pp. 856–860 (1976); R. O. Becker et al., "Treatment of Orthopedic Infections With Electrically-Generated Silver Ions," J. Bone & Joint Surgery, Vol. 60-A, pp. 871–881 (1978).

Silver and other metals are widely used in wound dressings and materials therefor. Fabo (U.S. Pat. No. 5,340,363) discloses a dressing that includes an outer absorbent layer and an inner porous, hydrophobic layer knitted of elastic threads and encapsulated by a soft, hydrophobic silicone or polyurethane gel. The gel can be used as a carrier for antibacterial agents such as zinc, pain-relieving substances, and agents that stimulate wound repair. Klippel et al. (U.S. Pat. No. 3,830,908) use micronized allantoin as a carrier for a bactericidal or bacteristatic ingredient (such as silver citro allantoinate) that is dispersed on the surface of a plastic air splint or other bandaging product. This material depends on the separation of the molecular moieties to provide the antibacterial action.

McKnight et al. (U.S. Pat. No. 3,800,792) disclose a surgical dressing having a layer of tanned, reconstituted collagen foam film laminated to a thin, continuous layer of an inert polymer. The collagen layer contains finely-divided silver metal added by soaking the collagen film in Tollen's reagent. Stowasser (U.S. Pat. No. 2,934,066) makes a dressing of absorbent, metal-coated fibers, such as a carding fleece coated with aluminum and backed by compressed cellulose, and polyamide fibers coated with vacuum-deposited silver.

Dressings for provision of electrical stimulation are also known. For example, Jones (U.S. Pat. No. 4,911,688) covers a wound with a clear cover that serves as a hollow chamber for holding a fluid such as saline in contact with a wound. When connected to a voltage source, a metal anode and a return electrode create free ions and an electrical field to enhance healing and tissue regeneration. Juhasz (U.S. Pat. No. 4,817,594) discloses a multi-layer dressing for covering discharging, malodorous wounds. The dressing includes a layer of an electrically-conductive material such as silver and a layer of charcoal fabric. Application of a DC (direct current) voltage to the conductive layer drives silver ions into the wound to enhance tissue growth and inhibit bacterial growth; application of transcutaneous AC (alternating current) is used for post-operative pain relief. Seiderman (U.S. Pat. No. 4,767,401) describes a bandage-like device used for iontophoretic administration of medicaments, including silver-protein colloids. The device includes a metal foil electrode (preferably aluminum), and makes use of the slight inherent negative electric charge proximate a wound site to generate a small electric field at the site.

Matson (U.S. Pat. No. 4,728,323) coats a substrate (nylon fabric, polymeric film, fiberglass, gauze or polyurethane foam) with a film of a silver salt deposited by vapor or sputter coating techniques. Alternatively, fibers can be coated and then woven or knitted into a fabric. Konikoff (U.S. Pat. No. 4,142,521) shows a bandage or surgical sponge material incorporating one or more electret elements, each electret providing a small electrostatic field to the area of the wound.

In U.S. application Ser. No. 08/524,134, filed Sep. 4, 1995, Becker et al. disclose a bimetallic fabric woven of nylon fibers coated with a first metal such as silver, interspaced at intervals with fibers coated with a second metal such as gold or platinum, preferably in a ratio of about 10:1. Alternatively, deposits of the second metal are placed on a fabric that contains the first metal. When contacted with an electrolyte, each contact junction between the first and second metals serves as a bimetallic junction that produces free silver ions. The material may be used in therapeutic or prophylactic treatment of wounds (including surgical incisions). An iontophoretic system for promoting tissue healing processes and inducing regeneration is described in Becker et al., U.S. application Ser. No. 08/623,046, filed Mar. 28, 1996. The system is implemented by placing a flexible, silver-containing anode in contact with the wound, placing a cathode on intact skin near the anode, and applying a wound-specific DC voltage between the anode and the cathode. Electrically-generated silver ions from the anode penetrate into the adjacent tissues and undergo a sequence of reactions leading to formation of a silver-collagen complex. This complex acts as a biological inducer to cause the formation in vivo of an adequate blastema to support regeneration. The above systems have limitations in that either an electrolyte or an external voltage source is required.

Regardless of whether silver is provided in the form of silver ions or as a topical composition (silver nitrate solution, silver sulfadiazine cream, or the like), its beneficial effects are manifested primarily at the treated surface and immediately adjacent tissues, and are limited by the achievable tissue concentration of silver ions. Despite the availability of numerous techniques for the delivery of silver and silver compounds in vitro and in vivo, there remains a need for a delivery system that is capable of supplying clinically useful concentrations of silver ions to a treatment site without the need for adjuvant electrical stimulation.

SUMMARY OF THE INVENTION

Accordingly, it is an object of the present invention to provide a wound dressing which can promote healing, stimulate cell growth, and alleviate pain.

The present invention provides a multilayer dressing in a variety of formats. The layers are comprised of metal, metal coated or non-metallic material and formed into a laminate structure. In a preferred embodiment the laminate comprises a number of layers of alternating silver and non-metallic layers of woven or nonwoven material.

BRIEF DESCRIPTION OF THE DRAWINGS

The invention is illustrated in the drawings in which like reference characters designate the same or similar parts throughout the figures of which:

FIG. 9 shows the data using *P. aeruginosa*.

FIG. 10 shows the data using *E. coli*.

FIG. 11 shows the data using *E. faecalis*.

FIG. 12 shows the data using *S. aureus*.

DESCRIPTION OF THE PREFERRED EMBODIMENTS

The present invention provides a multilayer laminate structure, wherein each layer preferably had a different composition, such that a gradient is formed by the layers. The structure is usable in contact with an area of skin 5 or other surface.

Figure 1:
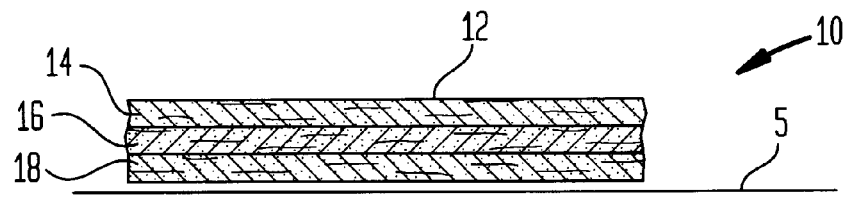
FIG. 1 is a schematic view in partial cutaway of the laminate structure of a preferred embodiment of the present invention.

In a first preferred embodiment, shown in FIG. 1, a multilayer laminate structure 10 is composed of at least two layers of a flexible material 12. In a preferred embodiment, three layers of material 14, 16 and 18, are utilized. Any number of layers is possible, depending on composition, thickness, denier, fiber density, and other characteristics. There are likely some practicable limits on the number of layers of material usable, such as where cost factors or material bulk outweigh the incremental benefits of an additional layer.

Each layer 14, 16 and 18 of flexible material 12 is preferably composed of a mixture of silver fibers and nonmetalized fibers. The silver is preferably of high purity, preferably from about 99.9% to about 99.999%, although lower purity levels can function in the present invention. High purity reduces the likelihood that contaminants or undesirable ions may contact or penetrate the wound or skin. The base fiber is preferably nylon, although other polymers or materials can be used with the present invention. The most important qualities of the base fiber are that it must be flexible and it must be capable of being coated with a metal or metals. In a preferred embodiment the base fiber is a fiber material that may be the same as the non-metalized fibers.

Each of the base fibers is substantially coated with metallic silver. Preferably, the fibers are 100% coated with metallic silver. The amount of coating may vary from about 5% to about 40% by weight, more preferably about 20% by weight. The silver fibers can be mixed with gold, platinum, ferromanganese, or mixtures of these materials. The metals that can be mixed with any metal that has a higher redox potential such as gold, platinum and ferromanganese.

The material can be formed according to methods known in to those skilled in the art, such as, but not limited to, oxidation-reduction reactions. The silver fibers are commercially available from Omnishield, Inc., Clarks Summit, Pa., Swift Metalizing Corp., Hartford, Conn., and Sauquoit Industries, Inc., Scranton, Pa. The denier of the silver fibers is in the range of from about 1 denier to about 30 denier, more preferably of from about 2 denier to about 8 denier, and still more preferably about 3 denier.

The nonmetalized fiber is preferably made of a material that produces a flexible fiber. The nonmetalized fiber can be a material, and such as, but not limited to, acetate, flax, glass, modacrylic, olefin polyester and polyethylenes, rubber, saran, spandex, vinyl, vinyon, cotton, wool, silk or other natural fiber, rayon, nylon, glasswool, acrylic, synthetic polymers, such as polyolefins sold under the trademarks DelNet, and Stringnet, other synthetic materials, blends or multicomponent fibers, either woven or nonwoven. The material chosen should be flexible, nonconductive, preferably biologically inert, flexible, nonconductive and also preferably nonimmunogenic. Since some individuals may have a topical hypersensitivity to certain fiber materials, the present invention can be designed so that nonallergenic or hypoallergenic materials are used, where desired. A preferred nonmetalized fiber is one of nylon, rayon, glass, silk, polyolefin or cotton. It is to be understood that other nonmetalized fiber materials can be used to achieve the objects of the present invention.

Preferably, the silver fibers and nonmetalized fibers are generally equally distributed throughout the material 12. In a preferred embodiment, the silver fibers are mixed with the nonmetalized fibers by air to create a random, generally uniform mixture of fibers. Alternatively, it is contemplated as being within the scope of the present invention to have areas of different fiber distribution for certain applications.

Figure 1A:
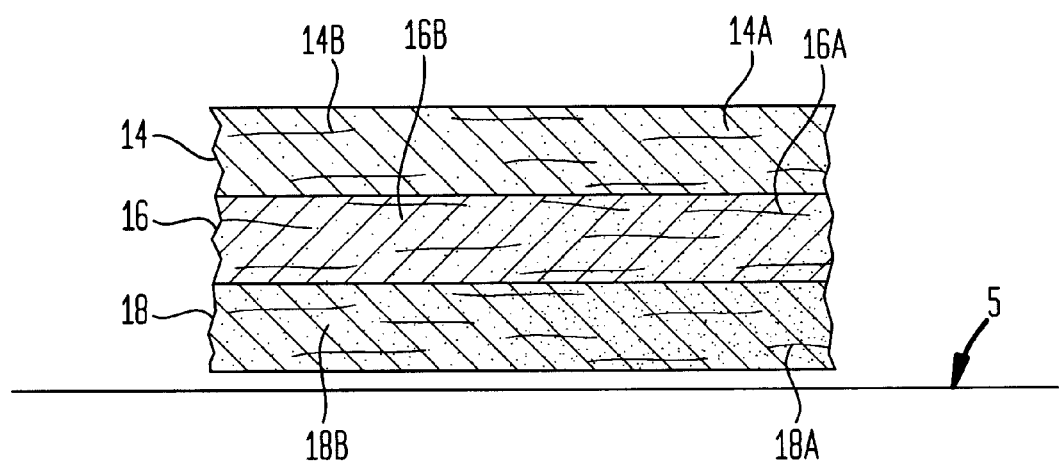
FIG. 1A is a side cutaway view of an alternative embodiment of the present invention showing a gradient of silver fiber concentration in the material, as shown by the increased stippling density.

FIG. 1A shows an alternative embodiment wherein at least one portion 14A, 16A or 18A has a higher average concentration or density of metalized fibers than a second portion 14B, 16B, or 18B of the material 12. Gradient concentration of mixed fibers can be made according to processes known to those of ordinary skill in the art. An application of a controlled fiber distribution is for a body cavity area dressing, such as, but not limited to, a vaginal or rectal area dressing.

The ratio of silver fibers to nonmetalized fibers is an important aspect of the present invention. In a given layer the ratio of silver fibers to nonmetalized fibers can be from about 1:100 to about 1:1 more preferably from about 1:50 to about 1:2, and still more preferably from about 1:20 to about 1:4. Where the layers are 100% silver nylon the ration would be about 1:0. The layers of material 12 are arranged so that the layer which will be in contact with the wound site will have the highest ratio, with a layer next removed from the wound site will have a lower ratio, and so forth. Thus, a decreasing concentration gradient is formed of silver fibers as one passes through layers of material 12 as one moves away from the wound site. In addition to a decreasing concentration gradient, the thickness of the layers preferably, although not mandatorily, increases as the distance from the skin increases; i.e., the thickness of the layer 14 next to the skin 5 is preferably less than the thickness of the layer 16 and 18 farther from the skin.

The layers 14, 16 and 18 can be laminated by sonic welding, adhesives, heated calendar rolls, needle punching, hydraulic needling or other fiber layer laminating or joining processes known to those of ordinary skill in the art. In a needle punching process, the layers are superimposed and passed through a pair of niprolls, one of the niprolls having series of spaced apart pins, needles or other protrusions extending radially therefrom, and the other niproll being smooth. The pins enter the fabric layer and push fibers from one layer into another layer, creating a physical bonding between the layers. After passing through the niproll assembly the laminate structure can be wound up on a take up roll or further processed.

The laminate structure 10 thus formed is semipermeable to most substances. The outermost layer is a semiocclusive membrane that permits gases such as air to pass but retards the rate of water loss. This property of the structure 10 maintains a relatively consistent water environment in the wound site area, which helps promote healing. In a preferred embodiment the structure 10 has a permeability to water vapor of the outer layer of from about 1000 grams/square meter/24 hours to about 3000 grams/square meter/24 hours. The water vapor loss for uncovered wounds can be as high as 5000 g/m2/24hr or 7,0000 g/m2/24hr in granulating wounds. The ideal permeability to water vapor is approximately 2500 g/m2/24hr.

Figure 2:
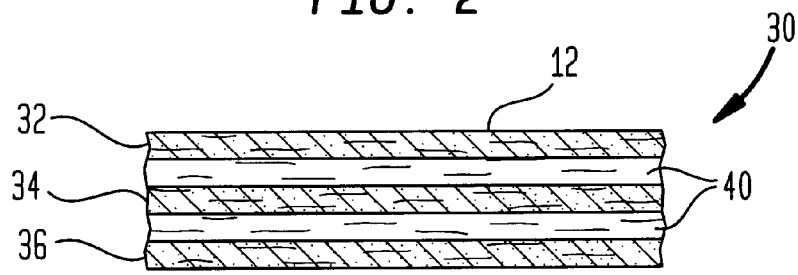
FIG. 2 is a schematic view in partial cutaway of the laminate structure of an alternative embodiment of the present invention.

In an alternative embodiment, shown in FIG. 2, a laminate structure 30 is comprised of layers 32, 34, and 36 of material 12. Between each layer is a layer of a nonconducting flexible material 40. This material 40 can be any flexible, porous material that is immunogenically inert and semipermeable. Such materials include, but are not limited to acetate, flax, glass, modacrylic, olefin polyester and polyethylenes, rubber, saran, spandex, vinyl, vinyon, cotton, wool, silk or other natural fiber, rayon, nylon, glasswool, acrylic, synthetic polymers polymers, such as polyolefins sold under the trademarks DelNet, and Stringnet, other synthetic materials, blends or multicomponent fibers, either woven or nonwoven. A preferred material is as DelNet®, a high density polyethylene blend available from Applied Extrusion Technologies, Inc., Middletown, Del. The use of the alternating layers of silver-containing material 12 and nonconducting material 30 creates a capacitor-like laminate, as will be described in greater detail hereinbelow.

The present invention is primarily usable as a dressing to promote wound healing by stimulating cell proliferation. The present invention also is usable as an antibacterial and antifungal. Surprisingly, the present invention also appears to have analgesic properties.

Figure 3:
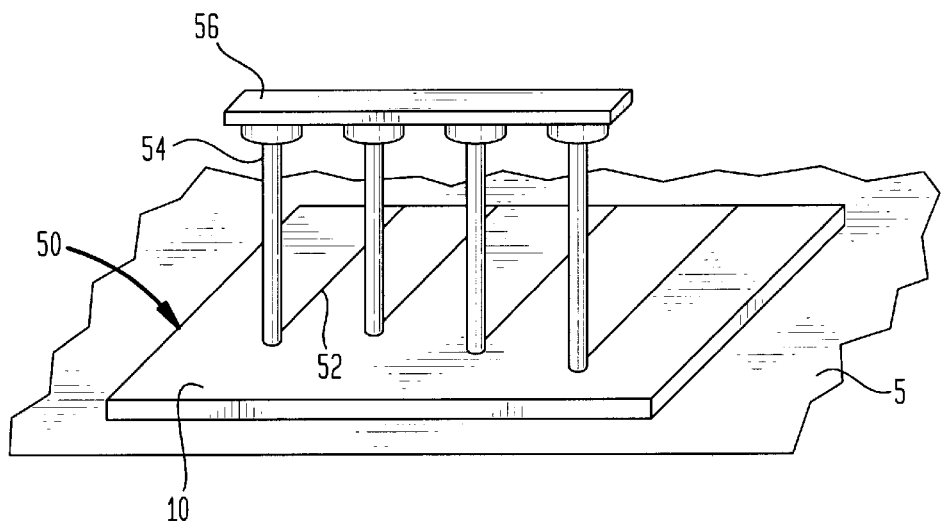
FIG. 3 is a schematic view of a dressing according to the present invention for use around an external fixature pin structure.

The laminate structure 10 or 30 of the present invention can be formed into any of a number of possible shapes, patterns or geometries, depending on the application and topography of the wound or application site. Several examples are shown in FIGS. 3–8. FIG. 3 shows a dressing 50 whereby a sheet of laminate 10 or 30 has a plurality of slits 52 defined therein. The dressing 50 is usable around an external set of fixture pins 54 that extend above the skin 5 and are maintained in place by a cross bar 56.

Figure 4A:
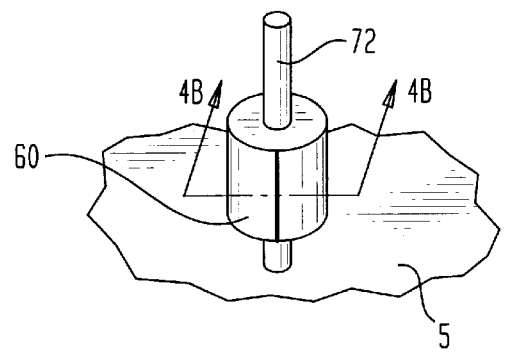
FIG. 4A is a schematic view of a dressing according to the present invention for use around a pin extending from the skin.
Figure 4B:
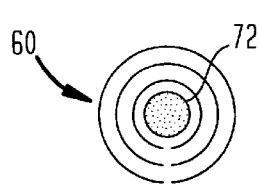
FIG. 4B is a cross section view of the dressing of FIG. 4A according to a first embodiment.
Figure 4C:
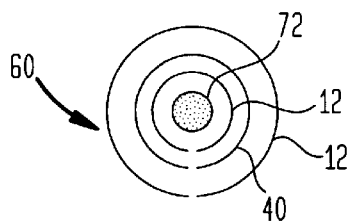
FIG. 4C is a cross section view of the dressing of FIG. 4A according to a second embodiment.

FIG. 4A shows a sleeve 60 made of the structure 10 or 30, which can be placed over a pin 72. FIG. 4B shows a cross-section of the sleeve 60 made of the structure 10, revealing the layers. FIG. 4C shows a cross-section of the sleeve 60 made of the structure 30, revealing the layers of alternating conductive and nonconductive materials 12 and 40, respectively.

Figure 5:
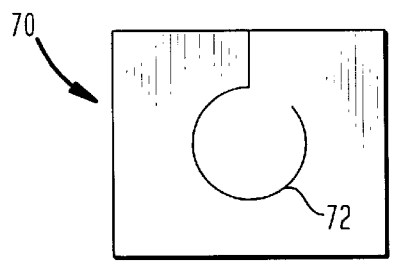
FIG. 5 is a schematic view of a dressing according to the present invention for use at an ostomy site.

FIG. 5 shows a dressing 70 with a semi-circular slit 72, usable as a dressing for an ostemy surgical site, or in conjunction with a feeding tube (not shown).

Figure 6:
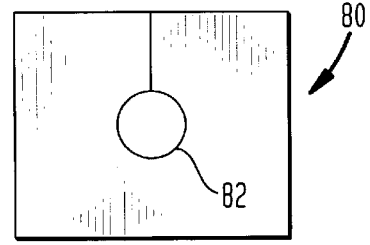
FIG. 6 is a schematic view of a dressing according to the present invention for use at a tracheostomy site.

FIG. 6 shows a dressing 80 with a circular opening 82, usable as a dressing for a tracheostomy surgical site.

Figure 7A:
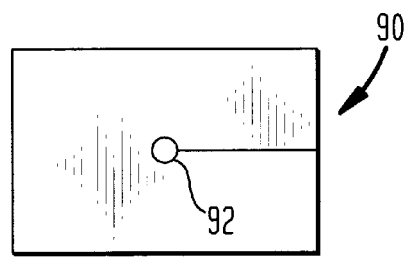
FIG. 7A is a schematic view of a dressing according to the present invention for use at an i.v. catheter site.
Figure 7B:
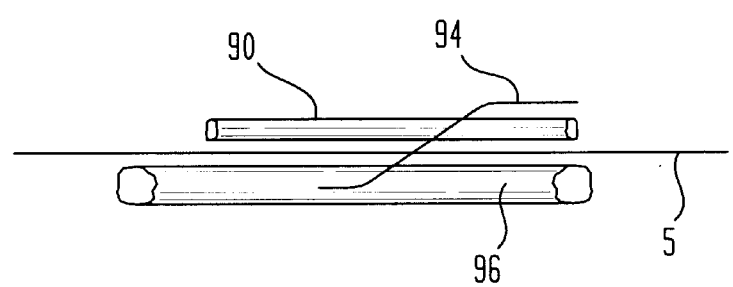
FIG. 7B is a schematic side view of a dressing according to FIG. 7A as shown in situ.

FIG. 7A shows a dressing 90, similar to dressing 80, but with a smaller opening 92, usable in conjunction with an i.v. catheter. FIG. 7B shows a catheter 94 inserted through the skin 5 in a vein 96. The dressing 90 is placed around the catheter 94.

Figure 8:
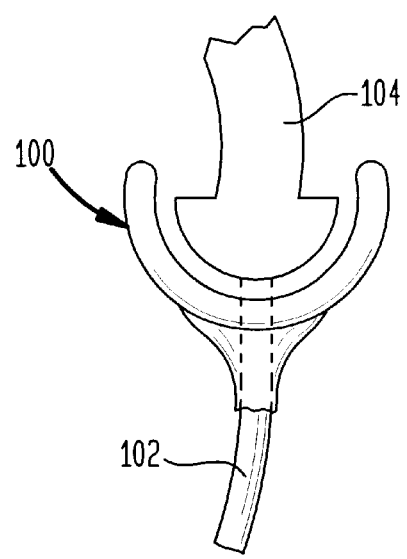
FIG. 8 is a schematic view of a dressing according to the present invention for use with a urinary catheter.
Figure 9:
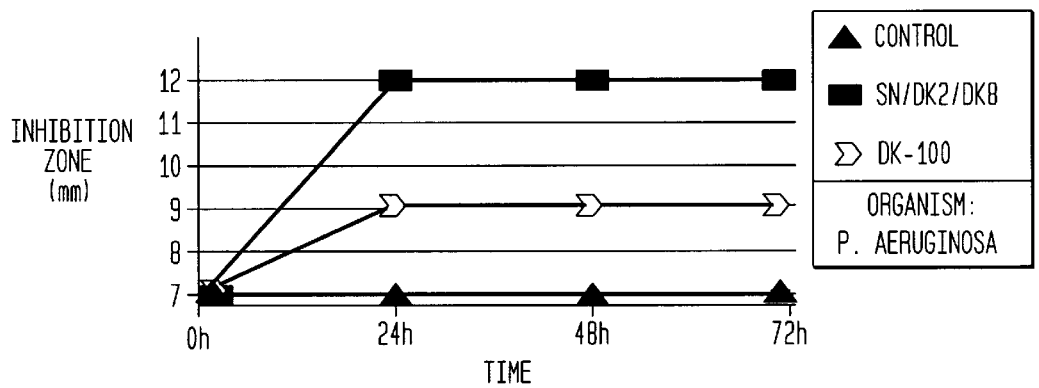
FIGS. 9–12 are graphs of the experimental data described in Example 1.
Figure 10:
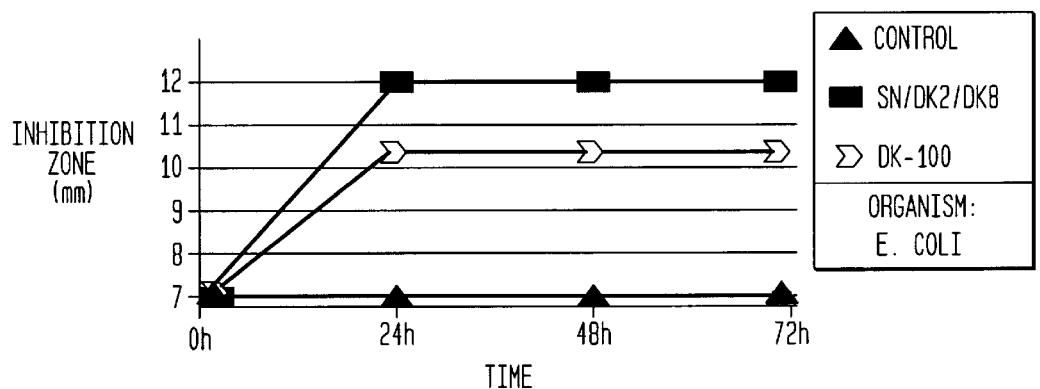
Figure 11:
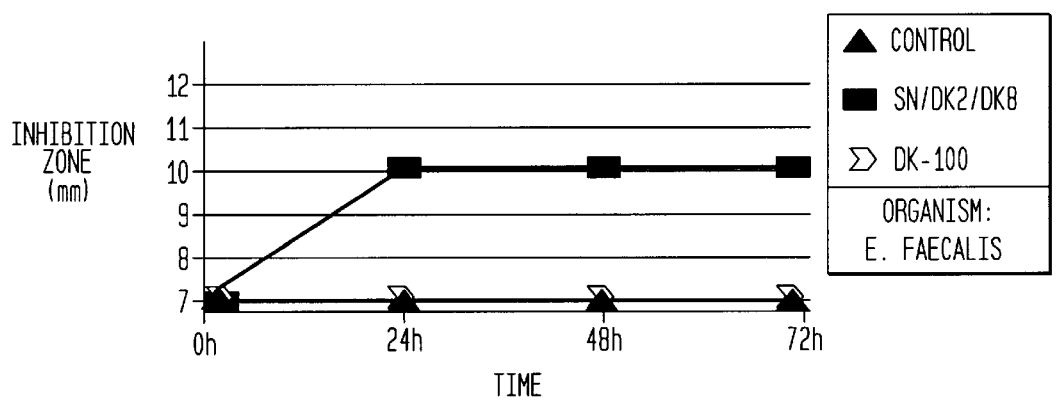
Figure 12:
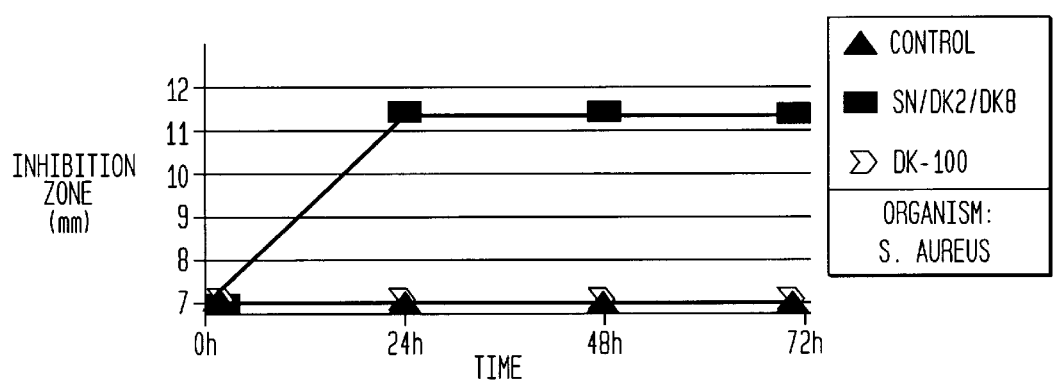
Figure 13:
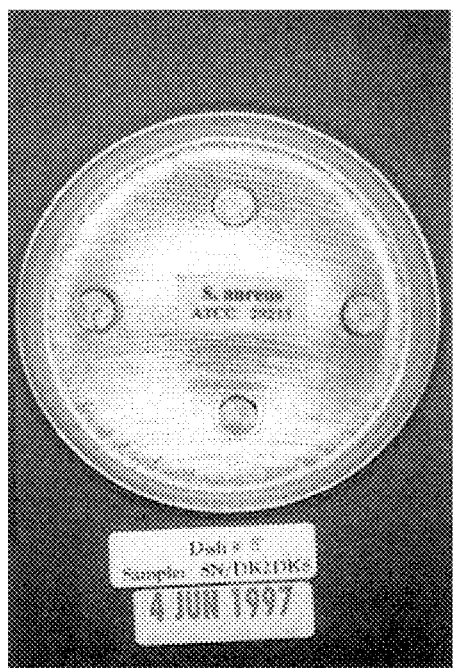
FIGS. 13–18 are photographs of different Petri dishes containing the labeled bacteria, showing the zones of inhibition.
Figure 14:
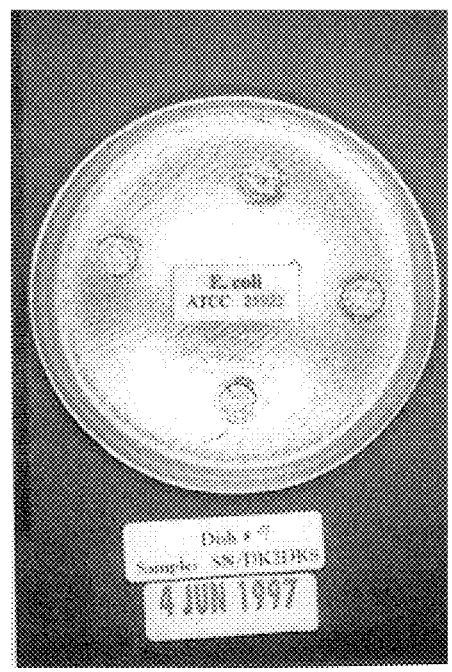
Figure 15:
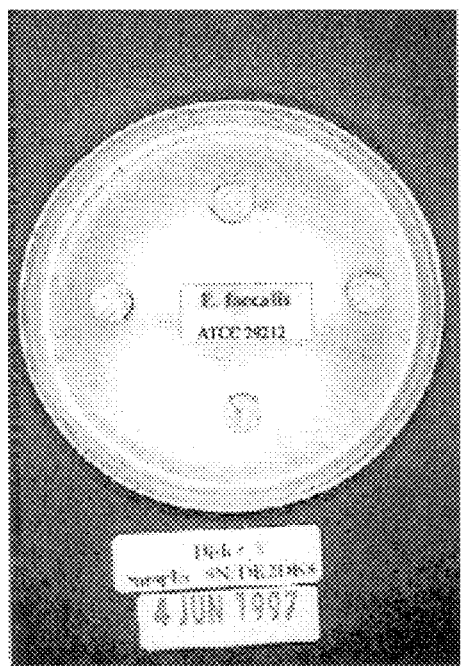
Figure 16:
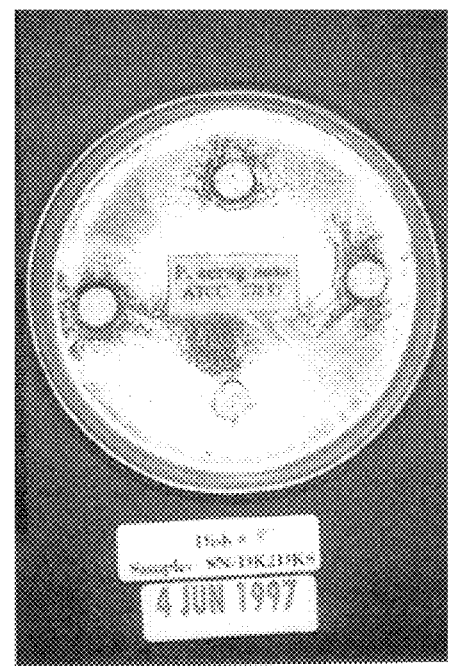
Figure 17:
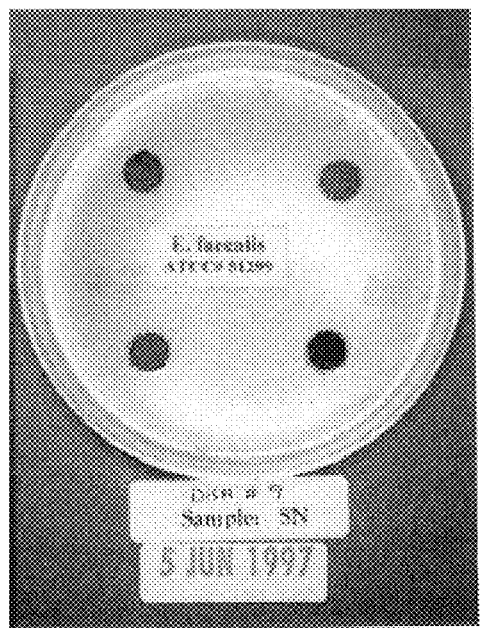
Figure 18:
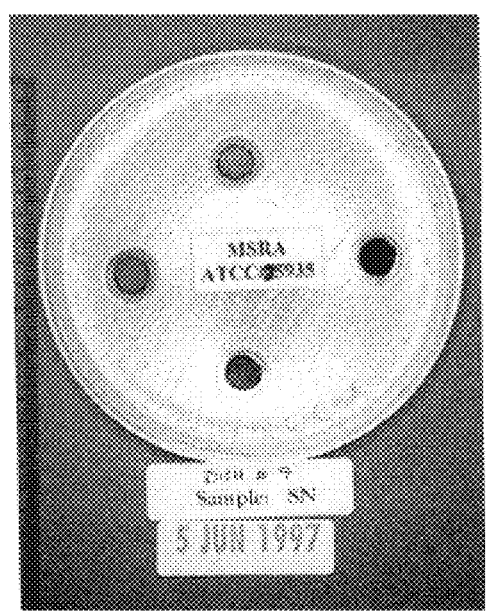
Figure 19:
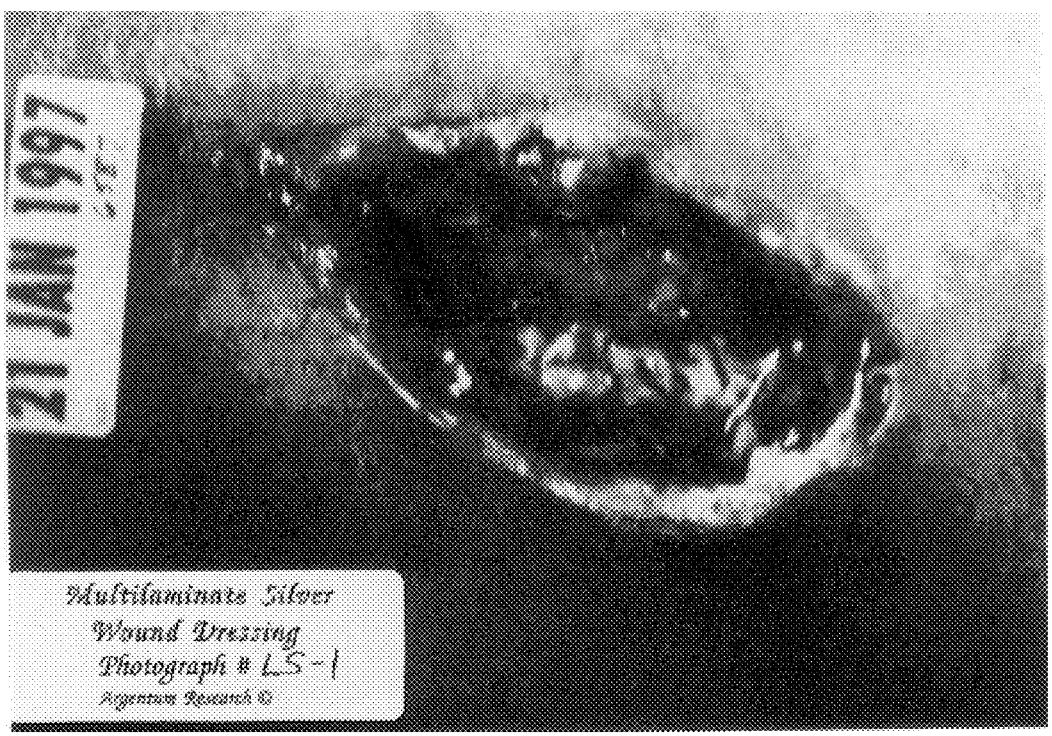
FIGS. 19–24 are photographs of a closeup of the wound of patient designated as LS as taken over a span of several months, showing the healing of the wound.
Figure 20:
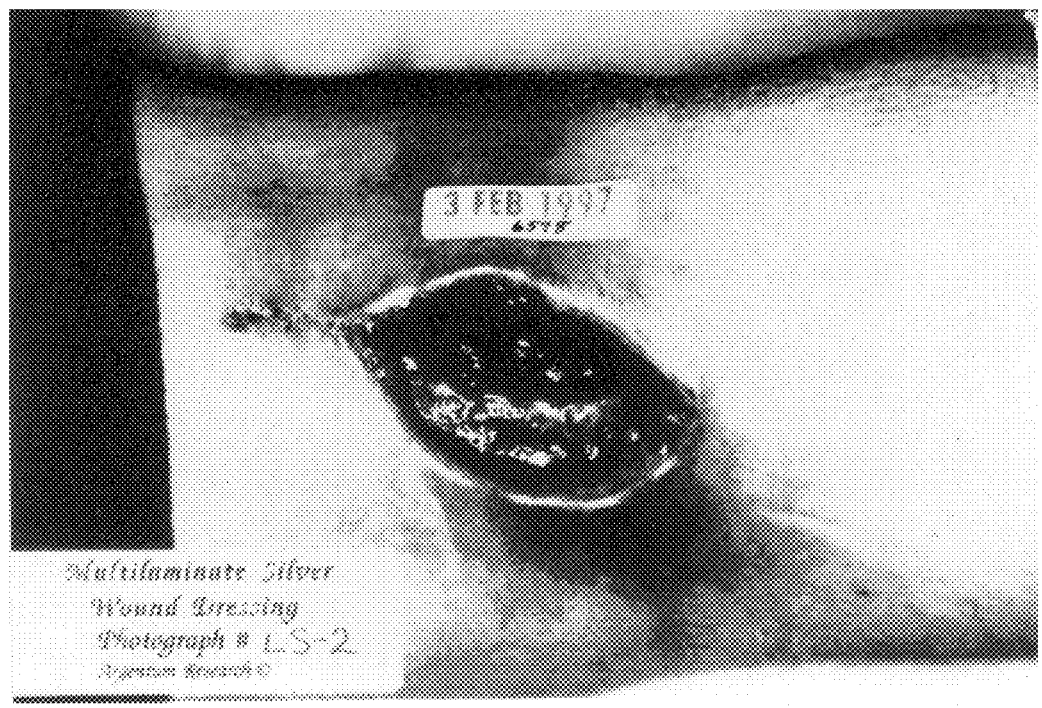
Figure 21:
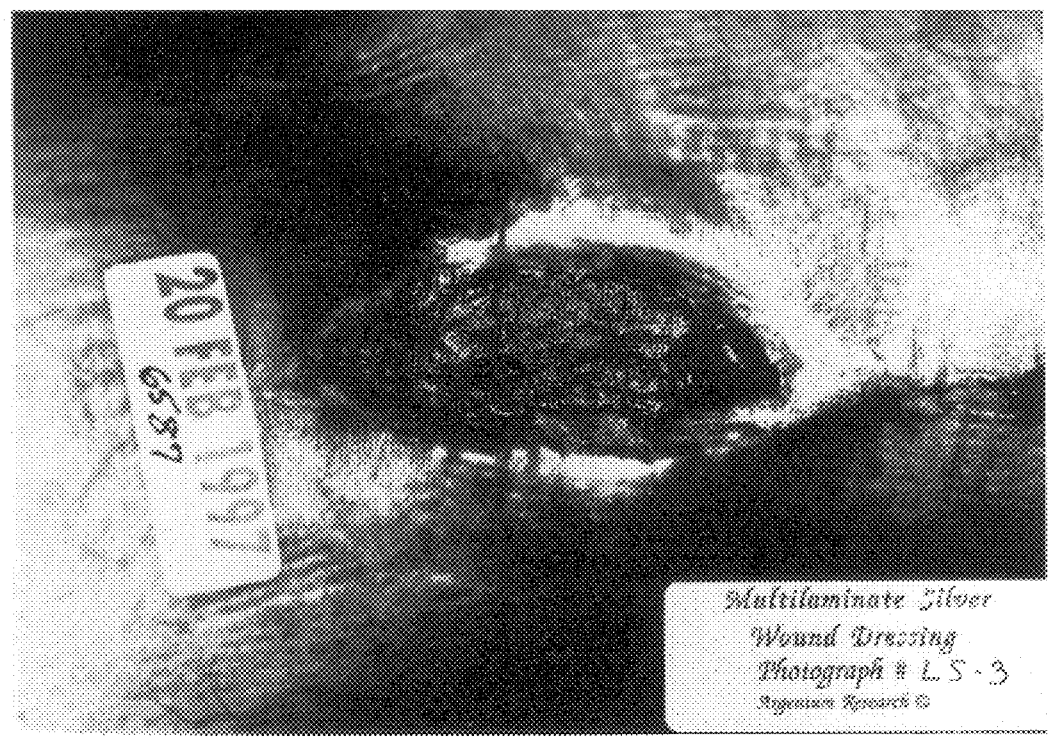
Figure 22:
Figure 23:
Figure 24:
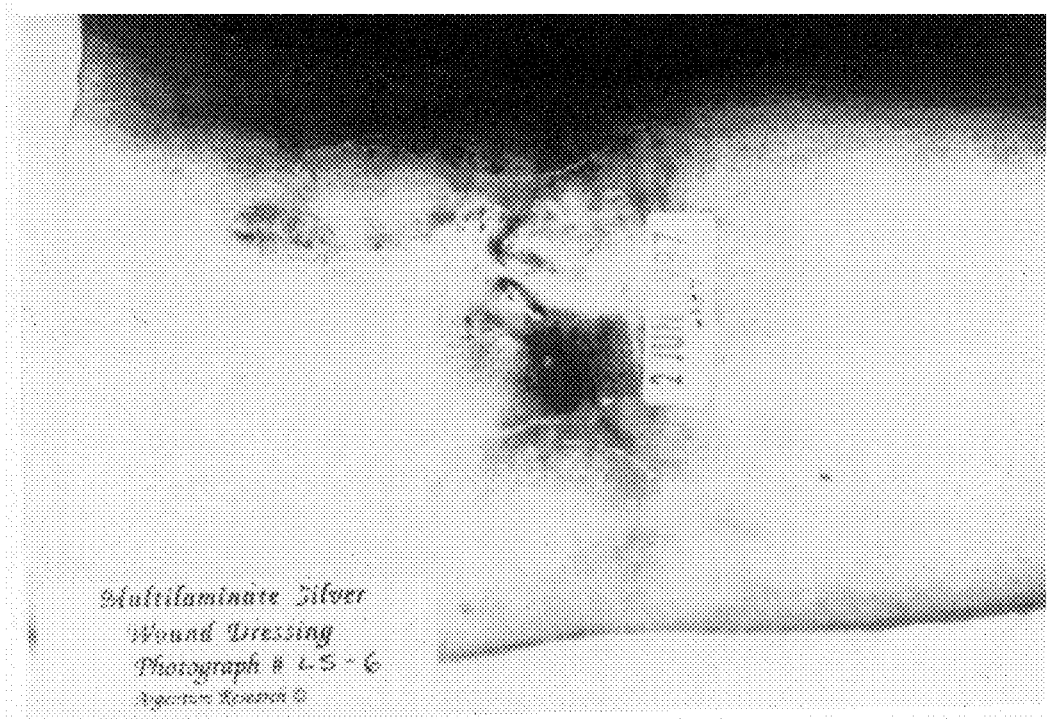
Figure 25:
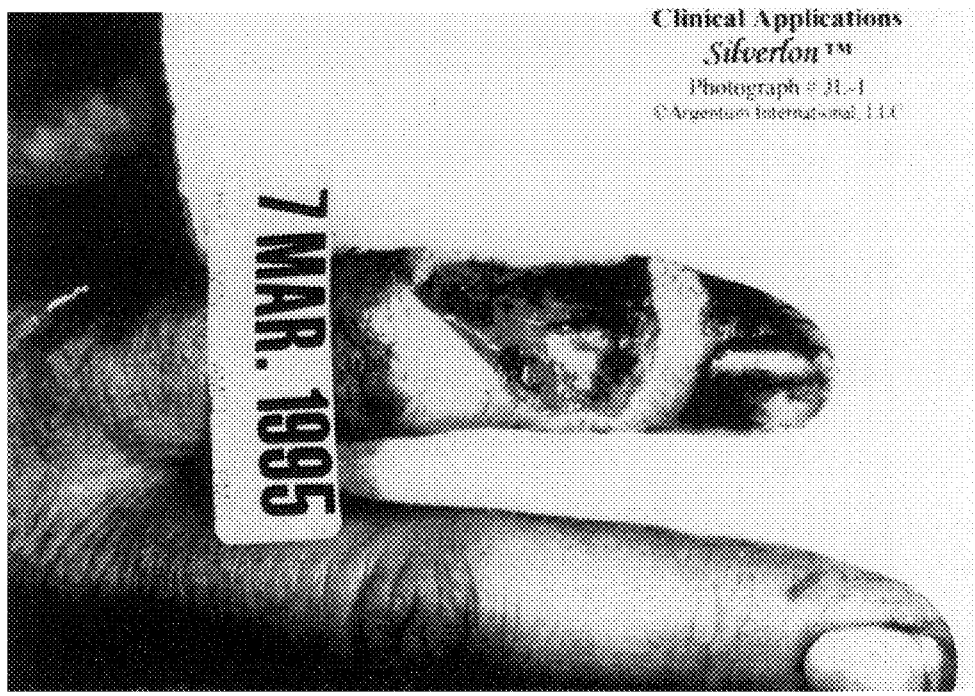
FIGS. 25–29 are photographs of a closeup of the wound of patient designated as JL as taken over a span of several months, showing the healing of the wound.
Figure 26:
Figure 27:
Figure 28:
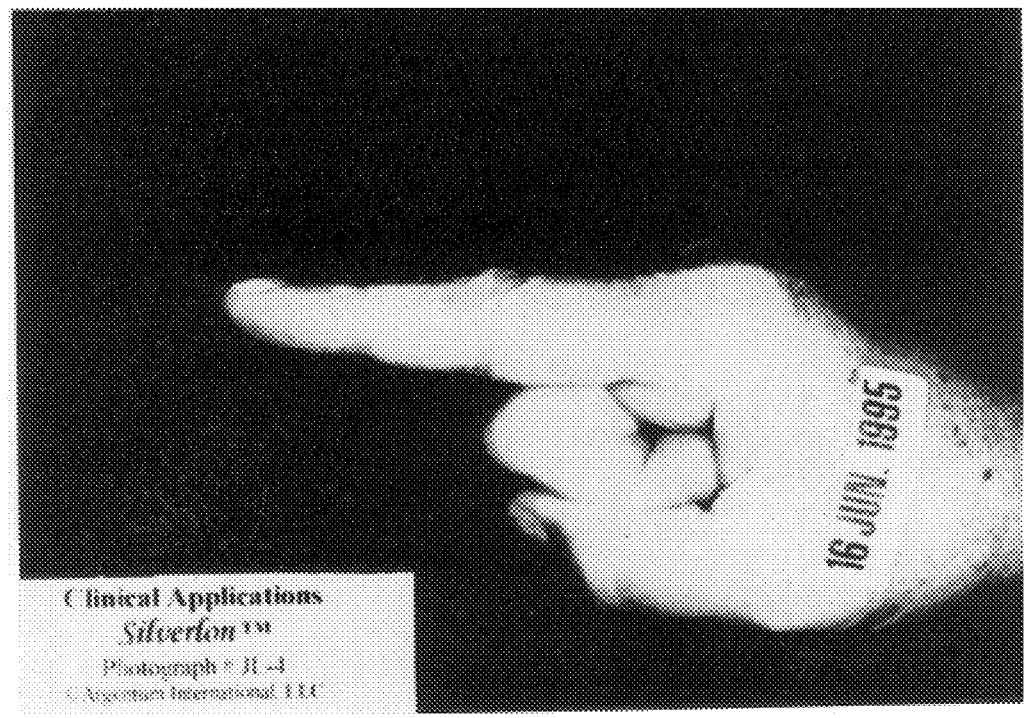
Figure 29:
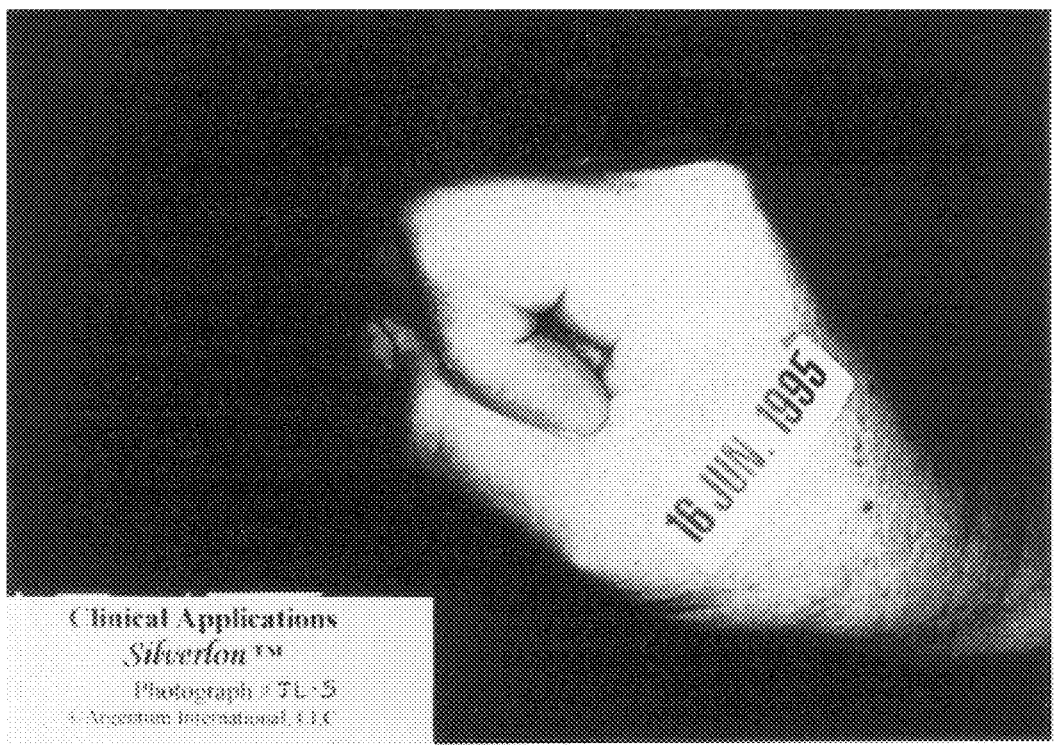

FIG. 8 shows a cup-shaped dressing 100, usable with a urinary catheter 102. The dressing 100 is fitted over the head of a penis 104 and taped or otherwise attached to the catheter 102.

The present invention can also be used as or in conjunction with an external post-labor and delivery vaginal pad, such as after an episotomy, or, around a cesaerian site. In general, the dressing can be applied to most post-operative wounds as well as most open wounds or burns.

The present invention can also be used as a wound drain, where the dressing is a layering of silver containing layers (100% silver-coated nylon) fibers alternating with a nonconductive material, such as but not limited to DelNet®. The layering can be two silver/nylon, between which is sandwiched a layer of DelNet®. A wound drain is different from a wound dressing in that the drain has silver coated fiber on both outer surfaces or with a layer of nonconducting material in between the nonconducting layer in between can be nylon, polyolefins, rayon, or the like.

Without desiring to be bound by a particular rationale or theory of operation, it is believed that the dressing of the present invention promotes wound healing by passively delivering silver ions present in the material 12 or 30 to and migrate into the wound and skin. The silver ions are formed from the passive dissolution of silver in an ionic form from metallic silver surface. This is different from the silver that is formed from chemical compounds in that silver is present in the wound as a salt when released from the compound form. In the silver that comes from metallic surfaces there is no salt present, only silver in a metallic form some of which is believed to be in the ionic form: i.e., a mixture of ionic and metallic forms of silver. The metallic form are clusters of silver ranging from 20 to 10,000 atoms clusters. An electrolyte is not required for release of silver from metallic forms only a liquid. The pain relieving aspect of the dressing should work in a dry wound but not the antibacterial aspect. The silver ions are believed to complex with cellular membrane structures, causing cellular alteration, and leading to cellular dedifferentiation. Undifferentiated cell proliferate faster than differentiated cells and are believed to have a longer lifespan because they are younger than differentiated cells. The proliferation of the undifferentiated cells leads to blastema formation and tissue regeneration. It is also believed that the present invention effects the cellular membrane potential, which changes the silver ion binding characteristics. This change causes the cell to transform to a dedifferentiated state, extending cell life and accelerating the cell proliferation.

A possible alternative theory of action is that the silver ions complex with collagen, producing a back electromotive force (EMF), which creates a battery effect, which in turn causes dedifferentiation. Silver ions are released from the silver coated base fibers by a process called oligodynamic action, i.e., the passive dissolution of silver in a crystalline form and in an ionic form into a solution. The process was first observed by a Swiss researcher in the 1890's that when metallic silver comes in contact with a water-containing liquid, a small ("oligo-") amount of silver is released into the solution ("dynamic"). The water-containing substance is an electrolyte-like fluid. Silver is typically not released on a completely dry wound absent other conditions.

Without wishing to be bound by any particular theory, two mechanisms of action may account for the pain relieving aspects of the dressing of the present invention. First, the silver may create an antibacterial environment, which in turn diminishes the inflammation caused by the bacteria and subsequently diminishes pain. Second, by separating the layers of silver nylon with a non-conducting material, a capacitative field may established by the current of injury that is present at the wound surface.

The dressing with the fastest pain relieving aspect is the one that layers 100% silver nylon with a non-conducting layer creating a laminate that is eight layers thick with the 100% silver layer against the wound surface (this composite will be called the MOD100% Ag/Non). When this dressing is placed against areas of blunt trauma such as contusions, sprains (stretched ligaments), and strains (torn muscles) it also provided pain relief. Testing four and six thickness in an alternating laminate pain relief was also found but not as rapid. The fact that the multilaminate MOD100% Ag/Non provided pain relief when the skin was intact suggests that the pain relieving aspect of the dressing is more an electrical phenomena, perhaps for the alteration in the electric field above the skin that is a result of damaged tissue beneath the skins surface.

An advantage of the present invention is that it does not require an external energy source in order to create and deliver silver ions, as some previous dressings reported in the prior art. The present invention provides a gradient effect, which acts as in a capacitor-like fashion, thereby increasing the effectiveness of the concentration of the silver ions delivered. A further advantage of the present invention is that it can be formed into a number of different useful structures forms, depending on the particular application. Additionally, by maintaining a cover on the dressing, the proper moisture environment in the treatment site is created and maintained, which further increases silver ion migration.

There is an improved degree of control, compared to previous systems, over the delivery and targeting of silver by the multiple layers and silver concentration gradient features of the present invention. The pain relieving characteristics of the dressing are improved by the addition of an non-conducting layer between the silver containing layers. The pain relieving effect is enhanced by making the silver containing layers out of 100% silver nylon.

Another advantage of the present invention is that, in contrast to antimicrobial creams, the dressing of the present invention creates a moisture environment with gas permeability that promotes healing, as opposed to a cream or emollient gas-impermeable barrier. The present invention is easier to replace and keep the wound site clean, rather than having to wash, rinse or otherwise traumatize the site to remove old creams or the like.

The invention will be further described in connection with the following examples, which are set forth for purposes of illustration only. Parts and percentages appearing in such examples are by weight unless otherwise stipulated.

EXAMPLES

Example 1

Laminate of Alternating Layers of Silver and DelNet

A dressing material was made of three layers. The layer that was against the bacterial culture called SN, was 100% silver plated nylon woven in a pattern of called warp knit with individual 15 denier fibers. The next layer was a non-woven 2 oz fabric composed of a mixture of 25% three denier silver plated fibers and 75% three denier rayon fibers. The third layer was a non-woven 8 oz fabric composed of a mixture of 5% three denier silver plated fibers and 95% three denier rayon fibers. The layers were laminated by needle punch. The ratio of the silver to nonmetalized fiber was as follows for each layer:

Layer 1 100% silver nylon
Layer 2 25% silver nylon to 75% nonmetalized fibers
Layer 3 5% silver nylon to 95% nonmetalized fibers The purpose of this Example is to determine the effectiveness of Silver Nylon Fabric Type "SNIDK2DK8" with Antimicrobial Disk Susceptibility Testing against four primary organisms that contribute to an infectious process warranting antimicrobial treatment.

Isolated colonies of each of four types of organisms that may play a pathogenic role were selected from primary agar plates and tested for susceptibility following NCCLS standards using the Disk diffusion Procedure (i.e., Kirby-Bauer Test). The goal is to evaluate the in vitro interactions between an isolated microbe and silver as an antimicrobial agent that would be appropriate for treatment of an infection in vivo.

Using a disk punch, silver nylon fabric was cut into disks measuring 7 mm in diameter. The disks were then dropped onto Mueller-Hinton Agar plates inoculated with each strain of bacterium to be tested. The plates were placed in a 37° C. incubator and were examined, measured, and photographed at 24, 48, 72, and 144 hour intervals.

The results of this project show the effectiveness of silver as an antimicrobial treatment.

Media; Reagents; Equipment

1. Bacterial isolates from the following QC organisms:

*Escherichia coli* ATCC: 25922

*Pseudomonas aeruginosa* ATCC: 27853

*Enterococcus faecalis* ATCC: 29212
*Staphylococcus aureus* ATCC: 29213
2. TSA II 5% Sheep Blood Agar plates for growth or the inoculum (nutrient nonselective agar plates incubated 18–24 hours.)
3. Colorimeter for adjusting the turbidity of the inoculum to meet NCCLS Standards.
4. 0.5 McFarland Standard for calibrating the colorimeter for gram positive organisms (i.e., *Enterococcus faecalis* and *Staphylococcus aureus*.
5. 1.0 McFarland Standard for calibrating the colorimeter for gram negative organisms (i.e., *Escherichia coli* and *Pseudomonas aeruginosa*).
6. Sterile Saline and Vortex mixer for suspension of the inoculum.
7. Mueller-Hinton II Agar plates from Lot #E2RXPG Exp. Jun. 23, 1997 that produces satisfactory quality control results. (This type of media most closely approximates the criteria for a reproducible medium).
8. Ruler and Template for measuring the diameters or inhibitory zones.
9. 7 mm Silver Nylon non-woven Fabric Disks containing 20% silver by wt.
10. 7 mm Disk Puncher
11. Camera for photographing plates.

Preparation of Inoculum

1. At least three to five well-isolated colonies of the same organism were selected from an agar plate culture. The top of each colony is touched with a sterile disposable polystyrene loop and the growth was transferred to a tube containing 1.8 ml of sterile saline.
2. The capped tubes containing the inoculum was vigorously agitated on a mechanical vortex mixer until a smooth suspension was achieved.
3. The tubes were placed in the colorimeter and the % T checked to met NCCLS Guidelines.
4. Within 15 minutes after adjusting the turbidity of the inoculum suspension to that of the standard and colorimeter, a sterile nontoxic cotton swab was dipped into the inoculum suspension and rotated several times with firm pressure on the inside wall of the tube to remove excess fluid.
5. The dried surface of a Mueller-Hinton Agar plate that had been brought to room temperature was inoculated by streaking the swab evenly distributing it over the entire agar surface. The lid of the dish was then replaced.
6. Three to five minutes was allowed for the surface of the agar to dry before the sample disks were added.
7. Four sample disks were added to each of the Mueller-Hinton plates with sterile tweezers.
8. A label stating the organism name was placed onto the center of each plate to be tested.
9. The plates were incubated at 37° C. for 24, 48, 72, and 144 hr. intervals.

With a metric ruler and a template, the zones of complete growth inhibition around each disk were carefully measured to within the nearest millimeters: the diameter of the disk was included in this measurement. The zones were measured at 24, 48 and 72 hour intervals. All measurements were made with the unaided eye while viewing the back of the petri dish with reflected light against a dark blue nonreflecting background. The plates were viewed from a directly vertical line of sight to avoid any parallax that that have resulted in misreadings.

After the 72 hr. reading, the "SN/DK2DK8" disks were removed with sterile tweezers and moved to a different area of growth on the plate. The plates were placed back into the incubator and re-examined after 144 hrs. The *E. coli, E. faecalis*. and *S. aureus* plates exhibited no sign of diminished zones of inhibition after the disks were removed from the original site. There were no new zones observed around the disks when placed in the new area of the plate. However, on the *P. aeruginosa* plates the zones of inhibition increased from 12 mm to 24 mm in the areas where the disks were removed and new zones of inhibition were formed around the disks after they were moved to a new area of the plate measuring 10 mm/72 hrs.

CLINICAL EXAMPLES

Clinical Case #1

FD is a 5 year old female who suffered partial thickness burns to the dorsal aspect of her right foot as a result of excessive sun exposure (sunburn). Antibiotic cream was applied that evening by the parents. Within 24 hours multilaminate silver dressings of the present invention were applied. The patient noted relief of the pain from the partial thickness burn within 30 minutes and slept the entire night pain free. The partial thickness burn healed within twenty four hours. No tattooing or scarring was present.

Clinical Case #2

RF is a 41 year old female who suffered partial thickness burns to the volar aspect of her forearm as a result of spilling boiling water on her forearm. The patient was seen in a local emergency room and silvadene cream applied and analgesics prescribed. Within 48 hours, multilaminate silver dressings of the present invention were applied. The patient noted relief of the pain of the burn within four hours and did not require any analgesics. She returned to the clinic in three days at which point the wound was completely healed. And the dressing were discontinued. The partial thickness burn healed within 48 hours.

Clinical Case #3

LS is a 44 year old female who suffered a postoperative wound infection and soft tissue breakdown in the popliteal fossa (back of knee). The day the dressing were initiated was noted in photograph #LS-1. Photograph #LS-2 was taken twelve days later with daily dressing changes. The patient noted that within forty eight hours the wound was essentially pain free with the exception when the dressing was changed and the wound was uncovered. Photograph #LS-3, #LS-4, and #LS-5 show progressive wound healing. Photograph #LS-6 shows the wound healed.

Clinical Care #4

JL is a 46 year old female who suffered a sharp laceration to the radial aspect of her index finger. Soft tissue was lost that extended down to the tendon (Photograph #JL-1). Dressings were changed on a daily basis. Photograph #JL-2 and #JL-3 show progressive wound healing. The patient noted that the wound was pain free after 48 hours. At the completion of wound healing (Photograph #JL-4 and #JL-5), the patient noted full range of motion of the digit with normal sensation to light touch.

The results of the Examples show that the multilayer laminate of the present invention clearly provides significantly improved benefits over a single silver layer dressing. While prior dressings may have incorporated more than one layer, they only contemplate the use of a single layer of silver-coated fibers. An unexpected result of the present invention is that multiple layers of silver, particularly where the layers are separated by nonconductive layers of material, provide improved silver ion migration and improved healing, antibacterial and antifungal properties.

Although only a few exemplary embodiments of this invention have been described in detail above, those skilled in the art will readily appreciate that many modifications are possible in the exemplary embodiments without materially departing from the novel teachings and advantages of this invention. Accordingly, all such modifications are intended to be included within the scope of this invention as defined in the following claims. In the claims, means plus function claims are intended to cover the structures described herein as performing the recited function and not only structural equivalents but also equivalent structures. Thus although a nail and a screw may not be structural equivalents in that a nail employs a cylindrical surface to secure wooden parts together, whereas a screw employs a helical surface, in the environment of fastening wooden parts, a nail and a screw may be equivalent structures.

It should further be noted that any patents, applications or publications referred to herein are incorporated by reference in their entirety.

What is claimed is:

1. A wound dressing, comprising a plurality of layers of a fibrous material, said material containing nonmetalized fibers and fibers that are at least partially coated with a metallic material to yield metalized fibers, each layer being joined to an adjacent layer and having a ratio of metalized fibers to nonmetalized fibers, wherein said layers form a gradient of metalized fiber to nonmetalized fiber ratios, the highest ratio layer capable of being placed in a contact with a wound site.

2. The wound dressing of claim 1, wherein said fibrous material is semi-permeable.

3. The wound dressing of claim 1, wherein said metalized fibers are at least partially coated with at least one material selected from the group consisting of silver, gold, platinum, and ferromanganese.

4. The wound dressing of claim 1, wherein said metalized fibers have a denier of from about 1 denier to about 30 denier.

5. The wound dressing of claim 1, wherein said metalized fibers have a denier of from about 2 denier to about 8 denier.

6. The wound dressing of claim 1, wherein said metalized fibers have a denier of about 3 denier.

7. The wound dressing of claim 1, wherein said nonmetalized fibers are made of a material that is flexible, biologically inert and nonconductive.

8. The wound dressing of claim 1, wherein said nonmetalized fibers are made of a material selected from the group consisting of cotton, wool, silk, other natural fiber, rayon, nylon, glasswool, acrylic and thermoplastic polymers.

9. The wound dressing of claim 1, wherein said nonmetalized fibers have a denier of from about 1 denier to about 30 denier.

10. The wound dressing of claim 1, wherein said nonmetalized fibers have a denier of from about 2 denier to about 8 denier.

11. The wound dressing of claim 1, wherein said ratio of metalized to nonmetalized fibers in said plurality of layers is from about 1:100 to about 1:1.

12. The wound dressing of claim 1, wherein said ratio of metalized to nonmetalized fibers in said plurality of layers is from about 1:50 to about 1:2.

13. The wound dressing of claim 1, wherein said ratio of metalized to nonmetalized fibers in said plurality of layers is from about 1:20 to about 1:4.

14. The wound dressing of claim 1, wherein said metalized and nonmetalized fibers are generally uniformly distributed throughout said material.

15. The wound dressing of claim 1, wherein said metalized and nonmetalized fibers are distributed in a gradient whereby at least one portion of said material has a higher average concentration of metalized fibers than a second portion of said material.

16. The wound dressing of claim 1, wherein said dressing comprises three layers of fibrous material, a first layer having a high relative ratio of metalized to nonmetalized fibers, a second layer laminated to said first layer and having a medium relative ratio of metalized to nonmetalized fibers, and a third layer laminated to said second layer and having a low relative ratio of metalized to nonmetalized fibers.

17. A wound dressing capable of being applied to a wound site, comprising:
   a) a first layer of a semipermeable fibrous material comprising a first ratio of metalized to nonmetalized fibers;
   b) a second layer of a semipermeable fibrous material comprising a second ratio of metalized to nonmetalized fibers;
   c) a third layer of a semipermeable fibrous material comprising a third ratio of metalized to nonmetalized fibers;
   wherein said first ratio layer is laminated to said second ratio layer and said second ratio layer is laminated to said third ratio layer so as to form a gradient of metalized to nonmetalized ratio layers, the highest ratio layer being capable of being in contact with a wound site, such that metal ion from said metalized fibers are capable of migrating towards and contact said wound site.

18. The wound dressing of claim 17, wherein said metalized fiber is comprised of silver.

19. A wound dressing, comprising: a plurality of laminated layers of a fibrous material, said material containing metalized fibers, each layer having a unique ratio of metalized fibers to nonmetalized fibers, a plurality of separating layers of a nonconductive porous material disposed between said layers of fibrous material, wherein said layers form a gradient of metalized fiber to nonmetalized fiber ratios, the highest ratio layer capable of being placed in contact with a wound site.

20. An antibacterial treatment for a dermal layer site, comprising: a plurality of laminated layers of a fibrous material, said material containing metalized fibers, each layer having a unique ratio of metalized fibers to nonmetalized fibers, a plurality of separating layers of a nonconductive porous material disposed between said layers of fibrous material, wherein said layers form a gradient of metalized fiber to nonmetalized fiber ratios, the highest ratio layer capable of being placed in contact with a wound site.

21. A method of treating a wound to promote healing, comprising:
   a) providing a wound dressing comprising a plurality of laminated layers of a fibrous material, said material containing metalized fibers, each layer having a unique ratio of metalized fibers to nonmetalized fibers, a plurality of separating layers of a nonconductive porous material disposed between said layers of fibrous material, wherein said layers form a gradient of metalized fiber to nonmetalized fiber ratios, the highest ratio layer capable of being placed in contact with a wound site; and,
   b) applying said dressing to a wound so that silver ions are capable of migrating to said wound and contact cells proximate to said wound.

22. A method of alleviating pain associated with a wound, comprising:

a) providing a wound dressing comprising a plurality of laminated layers of a fibrous material, said material containing metalized fibers, each layer having a unique ratio of metalized fibers to nonmetalized fibers, a plurality of separating layers of a nonconductive porous material disposed between said layers of fibrous material, wherein said layers form a gradient of metalized fiber to nonmetalized fiber ratios, the highest ratio layer capable of being placed in contact with a wound site; and, b) applying said dressing to a wound so that silver ions are capable of migrating to said wound and contact cells proximate to said wound.

23. A wound dressing, comprising:

a) at least one first layer of essentially silver fibers; and, b) at least one second layer of nonconductive fibers; said at least one first layer being laminated to said at least one second layer.

24. The wound dressing of claim 23, wherein said at least one first layer comprises eight layers and wherein said at least one second layer comprises eight layers, said first layers alternating with said second layers to form a laminate structure.

* * * * *